United States Patent [19]

Israel et al.

[11] 4,035,566
[45] July 12, 1977

[54] N-TRIFLUOROACETYLADRIAMYCIN-14-ALKANOATES AND THERAPEUTIC COMPOSITIONS CONTAINING SAME

[75] Inventors: Mervyn Israel, Needham; Edward J. Modest, Newton Centre, both of Mass.

[73] Assignee: Sidney Farber Cancer Institute, Inc., Boston, Mass.

[21] Appl. No.: 616,565

[22] Filed: Sept. 25, 1975

[51] Int. Cl.$^2$ .................................. C07H 15/20
[52] U.S. Cl. .................. 536/4; 424/180; 536/17; 536/119
[58] Field of Search ............... 260/210 AB, 210 R; 424/180; 536/4, 17

[56] References Cited
U.S. PATENT DOCUMENTS 3,803,124  4/1974  Arcamone et al. ......... 260/210 AB

*Primary Examiner*—Johnnie R. Brown

[57] ABSTRACT

Esters of $C_4$–$C_{10}$ saturated fatty acids with N-trifluoroacetyladriamycin are novel compounds. These compounds have the following structure:

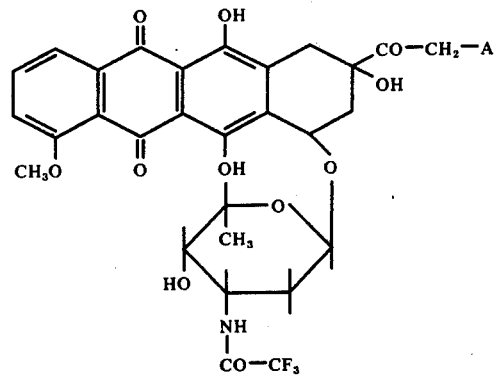

in which A is alkanoate having from 4 to 10 carbon atoms. Therapeutic compositions containing these compounds or the acetate or propionate of N-trifluoroacetyladriamycin are more effective than adriamycin in antitumor activity against murine P 388 and L 1210 leukemias and Ridgway osteogenic sarcoma in mice and at the same time significantly less toxic than adriamycin.

9 Claims, No Drawings

N-TRIFLUOROACETYLADRIAMYCIN-14-ALKANOATES AND THERAPEUTIC COMPOSITIONS CONTAINING SAME

The invention described herein was made in the course of work under a grant or award from the Department of Health, Education and Welfare.

This invention relates to certain novel chemical compounds having antitumor activity against murine p 388 and L 1210 leukemias and Ridgway osteogenic sarcoma in mice together with low toxicity and to therapeutic compositions, containing these compounds or certain related compounds together with a pharmaceutically acceptable non-toxic carrier, which are useful for administration to mice having certain tumors for extending their life spans.

Adriamycin[1] and daunomycin[2] and related compounds such as certain N-trifluoroacetyl derivatives have been described in U.S. Pat. Nos. 3,590,028 and 3,803,124. The latter patent also describes the preparation of N-trifluoroacetyladriamycin-14-acetate (identified by the name 14-acetoxy-N-trifluoroacetyldaunomycin) but does not indicate that this compound possesses any therapeutic or pharmacological activity and suggests no utility for it except its use in preparing N-trifluoroacetyladriamycin.

Adriamycin differs from daunomycin in that the former contains a hydroxyl group in the 14-position while the latter does not, having hydrogen instead. The structural formula of adriamycin is as follows:

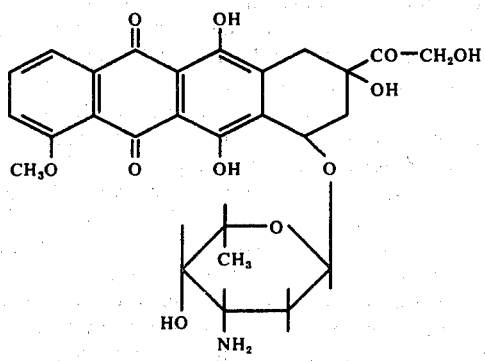

[1] Also known as doxorubicin.
[2] Also known as daunorubicin.

Adriamycin and daunomycin have both been found to possess antitumor activity and have been found to be effective clinically against certain malignant tumors: for example, for the induction of remission in acute leukemia; and adriamycin has shown clinical efficacy against certain solid tumors. They are among the most important agents used in chemotherapy of neoplastic disease. However, chemotherapy with adriamycin or daunomycin is accomplished by a variety of toxicities which limit the effectiveness of the compounds or of therapeutic compositions containing them as active agents, particularly limiting their long-term use.

The novel compounds of the present invention comprise N-trifluoroacetyladriamycin-14-alkanoates in which the alkanoate portion of the molecule contains from 4 to 10 carbon atoms. These compounds have the following structure:

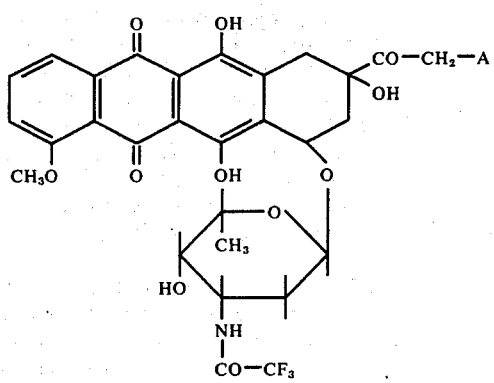

in which A is alkanoate having from 4 to 10 carbon atoms. Among such 14-alkanoates are butanoates such as isobutyrate, pentanoates such as valerate and pivalate, hexanoates such as caproate, as well as octanoates such as caprylate and decanoates such as caprate. These compounds, as well as the 14-acetate and 14-propionate compounds, have been found to be more effective in prolonging survival of tumor-bearing mice, carrying murine P 388 and L 1210 leukemias and Ridgway osteogenic sarcoma as well as to be significantly less toxic to mice than adriamycin or daunomycin in terms of pharmacological properties. Preferred are the butanoates, pentanoates and hexanoates, the most outstanding of the new compounds from a pharmacological standpoint being the pentanoates, in particular N-trifluoroacetyladriamycin-14-valerate. All of these compounds can also be named as 14-acyloxy-N-trifluoroacetyldaunomycins.

The novel compounds of the present invention as well as the 14-acetate and 14-propionate can be prepared from either adriamycin or daunomycin (or their salts such as the hydrochlorides) by several different procedures. For example, either adriamycin or daunomycin can be first converted to the N-trifluoroacetyl derivative. N-Trifluoroacetyladriamycin can be acylated directly to form the corresponding 14-alkanoate. N-Trifluoroacetyldaunomycin, on the other hand, can be iodinated to form 14-iodo-N-trifluoroacetyldaunomycin and the latter compound can be reacted with the alkali or alkaline earth metal salt of an appropriate fatty acid to form the desired 14-acyloxy-N-trifluoroacetyldaunomycin, that is, the desired N-trifluoroacetyladriamycin-14-alkanoate. In the alternative, daunomycin hydrochloride can be brominated to form 14-bromo-daunomycin hydrobromide, which in turn can be reacted with the salt of the desired fatty acid to form 14-acyloxy-daunomycin hydrochloride, then converted to 14-acyloxy-N-trifluoroacetyldaunomycin.

The preferred procedure involves preparing 14-iodo-N-trifluoroacetyldaunomycin as described in Arcamone et al. U.S. Pat. No. 3,803,124 and reacting it with an alkali metal or alkaline earth metal salt of the desired fatty acid, the sodium salt being preferred.

The therapeutic compositions of the present invention containing the novel compounds or the N-trifluoroacetyladriamycin-14-acetate or -14-propionate (that is, N-trifluoroacetyladriamycin-14-alkanoates in which the alkanoate portion of the molecule contains from 2 to 10 carbon atoms) as the active agents can be prepared by dispersing or dissolving the active agent in any pharmaceutically acceptable non-toxic carrier suitable for the desired mode of administration, which may be parenteral, that is, by injection which is intravenous, intramuscular, intraperitoneal, or other conventional mode. Suitable carriers include dimethyl sulfoxide, propylene glycol, glycerol, peanut oil, sesame oil, and, as preferred, a 10% by volume aqueous solution of polyoxyethylene sorbitan monooleate (polysorbate 80), sold under the trade name Tween 80, in which carrier the N-trifluoroacetyl-adriamycin-14-alkanoates are soluble to the extent of several milligrams per milliliter.

The toxicity and therapeutic effectiveness of the new compounds and active agents of the present invention are shown by in vitro assays and by in vivo evaluations in mice. The in vitro assays measure the growth inhibiting activity of the materials against the CCRF-CEM cell line in culture. The cell line was derived from the peripheral blood and a child with lymphoblastic leukemia as described by Foley et al., Cancer, Volume 18, page 522 et seq. (1965), and the assays were carried out by the procedure of Foley and Lazarus, Biochem. Pharmacol., Volume 16, pages 659 et seq. (1967), the results being reported in terms of the dose in micromoles per liter required to inhibit growth of the cultures by 50% relative to control cultures to which no drug had been added ($ID_{50}$). The in vivo evaluations were made by preparing a 0.2 to 0.7% by weight solution of the active agent in a 10% by volume aqueous solution of polyoxyethylene sorbitan monooleate (polysorbate 80) as a carrier and injecting the dosage intraperitoneally. The evaluations were made of the antitumor activity against the murine P 388 and murine L 1210 leukemias in $BDF_1$ male mice according to standard National Cancer Institute protocols as set forth by Geran et al., Cancer Chemotherap. Rep., Part 3, Volume 3, pages 1 et seq. (1972), except that a qd 1-4 schedule was used in place of qd 1-9 in order to conserve materials. Evaluations were also made of the antitumor activity against the Ridgway osteogenic sarcoma, a solid tumor, in $AKD_2/F_1$ mice, according to the procedures described in the report by G. J. D'Angio, C. L. Maddock, S. Farber, and B. L. Brown, Cancer Research, 25, 1002-1007 (1965).

Optimal dosage was determined by testing doses which were at several multiples of 10 milligrams/kilogram of body weight and the optimal dose was used for further tests. Some effectiveness can be observed at dosages ranging from 20 to 70 milligrams/kilogram of body weight, depending upon the particular ester employed.

The following examples are intended to illustrate more fully the preparation of the esters and their effectiveness without acting as a limitation upon the scope of the invention.

EXAMPLE 1

N-Trifluoroacetyladriamycin-14-valerate

A mixture of 1.65 g. of 14-iodo-N-trifluoroacetyldaunomycin, prepared and purified according to the procedure of Arcamone et al., U.S. Pat. No. 3,803,124, and 1.37 g. of sodium valerate in 165 ml. of anhydrous acetone was heated at reflux for 2 hours. The reaction mixture was cooled to room temperature and filtered, and the filter cake was washed with anhydrous acetone until the washings were no longer colored. The combined filtrate and washings were evaporated to dryness under reduced pressure. The residue was treated with a 1:1 mixture of water and chloroform (total volume 200 ml.), and the aqueous layer was separated and discarded. The chloroform extract was washed twice with cold water, once with aqueous pH 7 buffer, and finally with saturated aqueous sodium chloride. The chloroform solution was dried over sodium sulfate and the chloroform solvent was removed by evaporation under reduced pressure. The residue was dissolved in a small volume of chloroform and the product was precipitated by the addition of petroleum ether (b.p. 38°-49°). Three additional precipitations from chloroform and petroleum ether afforded 1.36 g. of N-trifluoroacetyladriamycin-14-valerate, m.p. 135°-136°, in analytical purity and homogeneous by thin layer chromatography (silica gel G; chloroform:methanol:water, 120:20:1 by volume) and high pressure liquid chromatography.

EXAMPLE 2

N-Trifluoroacetyladriamycin-14-valerate

14-Iodo-N-trifluoroacetyldaunomycin was prepared from daunomycin free base essentially according to the procedure of Example 1 but was not purified. 1.0 g. of crude 14-iodo-N-trifluoroacetyldaunomycin, containing N-trifluoroacetyldaunomycin and other impurities, in 100 ml. of anhydrous acetone was treated with 830 mg. of pulverized sodium valerate. The reaction mixture was heated at reflux for two hours, then cooled to room temperature and filtered. The filter cake was washed with anhydrous acetone until no color appeared in the washings. The combined filtrate and washings were evaporated to dryness under reduced pressure. The residue was partitioned between chloroform and water (1:1 mixture by volume, 200 ml. total volume). The chloroform layer was separated and was washed first with saturated sodium chloride solution, then with water, then with four portions of pH 7 aqueous buffer, and finally with saturated sodium chloride solution. The chloroform solution was dried over sodium sulfate and then was evaporated to dryness. The residue was dissolved in a small volume of chloroform. Addition of petroleum ether (b.p. 38°-49°) afforded 561.7 mg. of crude material, which was chromatographed on a silicic acid column. Elution with chloroform containing 0.75% ethanol gave 195 mg. of N-trifluoroacetyladriamycin-14-valerate, identical in all respects with material obtained according to Example 1. Further elution of the silicic acid column with chloroform containing ethyl acetate (10% by volume) gave 52.7 mg. of unchanged N-trifluoroacetyldaunomycin.

EXAMPLE 3

N-Trifluoroacetyladriamycin-14-propionate

A mixture of 37.5 mg. of 14-iodo-N-trifluoroacetyldaunomycin and 24.0 mg. of propionic acid sodium salt in 5.0 ml. of anhydrous acetone was heated at reflux for 2.5 hours. The reaction mixture was cooled to room temperature, and filtered. The filtrate was diluted with 25 ml. of chloroform and the chloroform solution was washed with cold water, then dried over sodium sulfate. The volume of the chloroform solution was reduced to about 2 ml., and this concentrate was chromatographed on a column of silicic acid. Elution with chloroform containing 0.75% ethanol afforded 18.6 mg. of N-trifluoroacetyladriamycin-14-propionate, m.p. 141°-143°.

EXAMPLE 4

N-Trifluoroacetyladriamycin-14-isobutyrate

A mixture of 250 mg. of 14-iodo-N-trifluoroacetyldaunomycin and 183.3 mg. of isobutyric acid sodium salt in 35 ml. of anhydrous acetone was heated at reflux for 2.5 hours. The reaction mixture was cooled to room temperature and filtered, and to the filtrate was added 100 ml. of chloroform. The chloroform solution was washed with three 25 ml. portions of cold water and then dried over sodium sulfate. The solution was evaporated to dryness under reduced pressure, and the residue was redissolved in 3–4 ml. of chloroform. The concentrate was chromatographed on a column of silicic acid. Elution with chloroform containing 20% ethyl acetate afforded, after evaporation of the solvent and drying of the product, 139 mg. of N-trifluoroacetyladriamycin-14-isobutyrate, m.p. 152°–153°.

EXAMPLE 5

N-Trifluoroacetyladriamycin-14-pivalate

A mixture of 37.5 mg. of 14-iodo-N-trifluoroacetyldaunomycin and 31.0 mg. of pivalic acid sodium salt in 5.0 ml. of anhydrous acetone was heated at reflux for 1.5 hours. The reaction mixture was cooled to room temperature and filtered, and to the filtrate was added 25 ml. of chloroform. The chloroform solution was washed with three 20 ml. portions of cold water, then dried over sodium sulfate. The solution was then evaporated to dryness under reduced pressure, and the residue was redissolved in 2 ml. of fresh chloroform. The concentrate was chromatographed on a column of silicic acid. Elution with chloroform containing 0.75% ethanol afforded 19.5 mg. of N-trifluoroacetyladriamycin-14-pivalate, m.p. 152°–153°.

EXAMPLE 6

N-Trifluoroacetyladriamycin-14-caproate

A mixture of 450 mg. of 14-iodo-N-trifluoroacetyldaunomycin and 414 mg. of caproic acid sodium salt in 50 ml. of anhydrous acetone was heated at reflux for 2 hours. The reaction mixture was cooled to room temperature and filtered. The filter cake was washed with 100 ml. of chloroform. The original filtrate and the chloroform washings were combined, and the organic phase was washed with three 20 ml. portions of cold water. the organic phase was dried over sodium sulfate, then evaporated to dryness under reduced pressure, and the residue redissolved in 4–5 ml. of chloroform. The chloroform solution was chromatographed on a column of silicic acid. Elution with chloroform containing 10% ethyl acetate afforded 252.5 mg. of N-trifluoroacetyladriamycin-14-caproate, m.p. 123.5°–125°. An additional 20.1 mg. of product was object when the column was eluted with chloroform containing 20% ethyl acetate.

EXAMPLE 7

N-Trifluoroacetyladriamycin-14-caprylate

A mixture of 150 mg. of 14-iodo-N-trifluoroacetyldaunomycin and 166 mg. of caprylic acid sodium salt in 20 ml. of anhydrous acetone was heated at reflux for 2 hours. The reaction mixture was cooled to room temperature and filtered, and to the filtrate was added 50 ml. of chloroform. The organic phase was washed with two 25 ml. portions of cold water, then dried over sodium sulfate. The solution was concentrated to a volume of 2–3 ml., which was chromatographed on a column of silicic acid. Elution with chloroform containing 0.75% ethanol afforded 93.2 mg. of N-trifluoroacetyladriamycin-14-caprylate, m.p. 108°110°.

EXAMPLE 8

N-Trifluoroacetyladriamycin-14-caprate

A mixture of 37.5 mg. of 14-iodo-N-trifluoroacetyldaunomycin and 48.5 mg. of capric acid sodium salt in 5.0 ml. of anhydrous acetone was heated at reflux for 2 hours. The reaction mixture was cooled to room temperature and filtered, and to the filtrate was added 25 ml. of chloroform. The chloroform solution was washed with cold water and dried over sodium sulfate. The dried solution was evaporated to dryness, and the residue was redissolved in 2.0 ml. of chloroform. The chloroform concentrate was chromatographed on a column of silicic acid. Elution with chloroform containing 0.75% ethanol afforded 19.4 mg. of N-trifluoroacetyladriamycin-14-caprate, m.p. 105°–107°.

EXAMPLE 9

N-Trifluoroacetyladriamycin-14-valerate

A suspension of 750 mg. of 14-bromodaunomycin hydrochloride, prepared as described in Arcamone et al. U.S. Pat. 3,803,124, and 2.48 g. of powdered sodium valerate in 520 ml. of anhydrous acetone was heated at reflux for 2 hours. The reaction mixture was cooled to room temperature and filtered. The filter cake was washed with anhydrous acetone until the washings were free of color. The combined filtrate and washings were evaporated to dryness under reduced pressure. The residue was dissolved in 150 ml. of 0.1 normal hydrochloric acid and the aqueous acid solution was extracted with three 50 ml. portions of chloroform to remove aglycone by-products. The aqueous layer, after the addition of 3 ml. of methanol, was extracted with four 25 ml. portions of 1-butanol. The butanol extracts were combined and evaporated under reduced pressure at 35° until no further distillate appeared. Filtration of the suspension at this point afforded, after thorough washing with ethyl acetate and drying, 347.7 mg. of adriamycin-14-valerate hydrochloride, m.p. 176°–177°. A second crop of 62.2 mg. of product was obtained from further concentration of the filtrate at a somewhat higher temperature. Both crops of material were of high purity by thin layer chromatographic analysis (silica gel G plates; solvent system: chloroform:methanol:water, 100:20:1 by volume).

A suspension of 300 mg. of adriamycin-14-valerate hydrochloride in 20 ml. of ethyl acetate was treated with 0.45 ml. of trifluoroacetic anhydride in small portions over a few minutes until all solids had dissolved. The solution was mixed immediately with equal portions of water and chloroform (total volume 100 ml.). The chloroform layer was separated and washed once with water and twice with pH 7 aqueous buffer. The chloroform solution was dried over sodium sulfate and then was evaporated to dryness under reduced pressure. The residue was dissolved in 25 ml. of methanol, and the resulting solution was heated at reflux for 5 minutes, then cooled and evaporated to dryness. The residue was redissolved in 4 ml. of chloroform, and the crude product was precipitated by the addition of 20 ml. of petroleum ether (b.p. 38°–49°). The crude material was purified by chromatography on a silicic acid column. Elution with chloroform containing 0.75% ethanol afforded 181 mg. of N-trifluoroacetyladriamycin-14-valerate, identical chromatographically and by spectral comparison with samples of product prepared as described in Examples 1 and 2.

EXAMPLE 10

N-Trifluoroacetyladriamycin-14-valerate

A suspension of 193.4 mg. of adriamycin free base in 20 ml. of methylene chloride and 20 ml. of dry dioxane was treated with 1.2 ml. of trifluoroacetic anhydride with stirring at room temperature. The clear solution was diluted with chloroform and the organic layer was extracted with water. The chloroform solution was then washed with two 20 ml. portions of aqueous pH 10 buffer, and then was dried over sodium sulfate. The dried chloroform solution was evaporated under reduced pressure. The residue was dissolved in 40 ml. of methanol, and the methanol solution was heated at reflux for 5 minutes. The methanol solvent was then evaporated to dryness to give a residue which weighed 189.3 mg. Of this residue 170 mg. was purified by chromatography on a column of silicic acid. Elution with chloroform containing 20% ethyl acetate by volume afforded 90.8 mg. of pure N-trifluoroacetyladriamycin.

A solution containing 5.0 mg. of N-trifluoroacetyladriamycin dissolved in 0.5 ml. of anhydrous pyridine was treated with 18 microliters of valeroyl chloride, which was added in small portions over a two-day period. The reaction was monitored by thin layer chromatography and when the presence of N-trifluoroacetyladriamycin could no longer be observed, the reaction mixture was diluted with 10 ml. of chloroform. The chloroform solution was extracted three times with pH 4 gaseous buffer and once with pH 7 buffer. The dried chloroform solution was then evaporated under reduced pressure, and the residue was purified by preparative thin layer chromatography on silica gel G with chloroform:methanol:water (120:20:1 by volume) as the solvent system. The major orange-colored band was removed and washed free of silica gel with a mixture of methanol and ethyl acetate. Upon evaporation of the methanol and ethyl acetate, 2.19 mg. of N-trifluoroacetyladriamycin-14-valerate was obtained. This material was idential by spectral and chromatographic comparison with samples of N-trifluoroacetyladriamycin-14-valerate prepared by the earlier described methods.

The following table summarizes the inhibitory activity of various N-trifluoroacetyladriamycin-14-alkanoates as well as other materials when tested in vitro as described in the paragraphs preceding Example 1 above.

TABLE I

| Compound | $ID_{50}$ Micromoles per liter |
|---|---|
| Adriamycin | 0.066 |
| Daunomycin | 0.035 |
| N-Trifluoroacetyl-adriamycin-14-alkanoates | |
| Acetate | 0.20 |
| Propionate | 0.30 |
| Isobutyrate | 0.28 |
| Valerate | 0.24 |
| Pivalate | 0.59 |
| Caproate | 0.33 |
| Caprylate | 0.36 |
| Caprate | 0.39 |

The results show the relatively low toxicity of all of the N-trifluoroacetyladriamycin-14-alkanoates as compared to adriamycin or daunomycin.

The following table summarizes the in vivo antitumor activity against murine P 388 leukemia tested by the Geran et al. procedure as exampled above:

TABLE II

| Compound | Optimal dose mg/kg of body wt. | percent MILS* | Survivors 30da | 60da |
|---|---|---|---|---|
| None | — | 0 | 0/15 | |
| Adriamycin | 4.0 | 132 | 0/6 | |
| Daunomycin | 2.0 | 91 | 0/6 | |
| N-Trifluoroacetyl-adriamycin-14-alkanoates | | | | |
| Acetate | 40 | 173 | 2/5 | 0/5 |
| Isobutyrate | 40 | 150 | 3/5 | 1/5 |
| Valerate | 40 | 429 | 4/5 | 3/5 |
| Caproate | 60 | 271 | 5/5 | 1/5 |
| Caprylate | 60 | 243 | 5/5 | 1/5 |

*Median Increase in Life Span Compared with Untreated Mice

Although adriamycin is toxic at and above a dose of 4 mg/kg under these test conditions, no toxicity was observed with the caproate and caprylate at a dose of 60 mg/kg.

The murine L 1210 leukemia is generally poorly responsive to chemotherapy. Adriamycin is only moderately effective, and daunomycin much less so, in prolonging survival of mice bearing this tumor. The following table summarizes the results of three separate in vivo tests of N-trifluoroacetyladriamycin-14-valerate against murine L 1210 leukemia following the Geran et al. procedure as described above:

TABLE III

| Compound | Optimal dose mg/kg of body wt. | Percent MILS | Survivors 30da | 60da |
|---|---|---|---|---|
| None | — | 0 | 0/15 | |
| Adriamycin | 4.0 | 45 | 0/5 | |
| N-Trifluoroacetyl-adriamycin-14-valerate | 60.0 | > 445[a] | 4/5 | 4/5[b] |
| " | 70.0 | > 445[a] | 4/5 | 4/5[b] |
| Adriamycin | 4.0 | 54 | 1/5 | 0/5 |
| N-Trifluoroacetyl-adriamycin-14-valerate | 50.0 | > 445[a] | 4/7 | 4/7[c] |
| " | 60.0 | > 445[a] | 3/6 | 3/6[c] |
| Adriamycin | 4.0 | 42 | 0/7 | |
| N-Trifluoroacetyl-adriamycin-14-valerate | 50.0 | > 400 | 5/7 | 5/7[d] |
| " | 60.0 | > 400 | 6/7 | 6/7[d] |

[a] Calculated as of day 60.
[b] All 60-day survivors alive and well out past one year.
[c] One animal at each dose level sacrificed on day 120 for histology; remaining survivors alive and well out past one year.
[d] One animal at each dose level sacrificed on day 65 for histology; remaining survivors alive and well out past day 250.

In vivo tests of adriamycin-14-valerate against L1210 leukemia under the same conditions showed it to be no more effective than daunomycin (no survivors after 30 days) in prolonging survival of tumor-bearing mice; it displayed toxicity at doses above 4.0 mg/kg on the qd 1–4 schedule.

The following table summarizes the in vivo antitumor activity of N-trifluoroacetyladriamycin-14-valerate against the murine Ridgway osteogenic sarcoma following the D'Angio et at. procedure as described above:

TABLE IV

| Compound | Dose mg/kg | Schedule, days* | Median Survival, days | Percent MILS |
|---|---|---|---|---|
| None | — | — | 36.5 | 0 |
| Adriamycin | 3.0 | 16–19 | 51.0 | 40 |
| N-trifluoro-acetyl-adriamycin-14-valerate | 50.0 | 16–19 | 84.0 | 130 |
| N-Trifluoro-acetyl-adriamycin-14-valerate | 60.0 | 16–19 | 81.0 | 122 |

*Therapy was started on day 16 when the intramuscularly implanted tumor was palpable. Seven mice were used in each group, and all compounds were administered intraperitoneally.

In addition to the prolonged survival seen in mice bearing the solid Ridgway tumor and treated with N-trifluoroacetyladriamycin-14-valerate, the gross number of complete remissions was greater and the median duration of complete remission was longer than in similar tumor-bearing mice treated with adriamycin. Complete remission in this system is defined as the absence of palpable tumor.

What is claimed is:

1. N-trifluoroacetyladriamycin-14-alkanoates in which the alkanoate portion of the molecule contains from 4 to 10 carbon atoms.
2. The compound claimed in claim 1 in which the alkanoate is pentanoate.
3. The compound claimed in claim 1 in which the alkanoate is valerate.
4. The compound claimed in claim 1 in which the alkanoate is butanoate.
5. The compound claimed in claim 1 in which the alkanoate is isobutyrate.
6. The compound claimed in claim 1 in which the alkanoate is hexanoate.
7. The compound claimed in claim 1 in which the alkanoate is caproate.
8. The compound claimed in claim 1 in which the alkanoate is octanoate.
9. The compound claimed in claim 1 in which the alkanoate is caprylate.

* * * * *

UNITED STATES PATENT AND TRADEMARK OFFICE
CERTIFICATE OF CORRECTION

PATENT NO. : 4,035,566

DATED : July 12, 1977

INVENTOR(S) : Mervyn Israel and Edward J. Modest

It is certified that error appears in the above-identified patent and that said Letters Patent are hereby corrected as shown below:

Col. 1, line 59, "accomplished" should be --accompanied--;

Col. 5, line 47, "water.the" should be --water.  The--;

Col. 5, line 55, "object" should be --obtained--;

Col. 6, line 3, "108°110°" should be --108°-110°--;

Col. 7, line 32, "gaseous" should be --aqueous--;

Col. 7, line 42, "identical" is misspelled;

Col. 8, line 3, "exampled" should be --explained--;

Col. 8, Table III, line 45, "42" should be under the column headed "Percent MILS" and "0/7" should be under the column headed "Survivors-30da";

Col. 8, line 67, "at." should be --al.--;

Col. 9, Table IV, line 5, "N-trifluoro-" should be --N-Trifluoro- --.

Signed and Sealed this

Fourth Day of October 1977

[SEAL]

Attest:

RUTH C. MASON
*Attesting Officer*

LUTRELLE F. PARKER
*Acting Commissioner of Patents and Trademarks*